(12) United States Patent
Shimp

(10) Patent No.: US 7,399,739 B2
(45) Date of Patent: Jul. 15, 2008

(54) VERTEBRAL AUGMENTATION COMPOSITION AND METHOD

(75) Inventor: Lawrence A. Shimp, Morganville, NJ (US)

(73) Assignee: Osteotech, Inc., Eatontown, NJ (US)

( * ) Notice: Subject to any disclaimer, the term of this patent is extended or adjusted under 35 U.S.C. 154(b) by 743 days.

(21) Appl. No.: 10/399,423

(22) PCT Filed: Oct. 23, 2001

(86) PCT No.: PCT/US01/51019

§ 371 (c)(1),
(2), (4) Date: Oct. 20, 2003

(87) PCT Pub. No.: WO02/34309

PCT Pub. Date: May 2, 2002

(65) Prior Publication Data

US 2004/0052829 A1    Mar. 18, 2004

(51) Int. Cl.
*A61K 38/00*    (2006.01)
*A61K 9/14*    (2006.01)
*A61K 35/32*    (2006.01)
*A61K 33/42*    (2006.01)
*A61F 2/02*    (2006.01)

(52) U.S. Cl. ............... 514/2; 424/423; 424/487; 424/488; 424/549; 424/602

(58) Field of Classification Search ............... None
See application file for complete search history.

(56) References Cited

U.S. PATENT DOCUMENTS 5,484,601 A    1/1996    McBrayer et al.
2003/0031698 A1*    2/2003    Roeder et al. ............... 424/423

FOREIGN PATENT DOCUMENTS

WO    99/18894    4/1999
WO    01/54746    8/2001

\* cited by examiner

*Primary Examiner*—Raymond J. Henley, III
(74) *Attorney, Agent, or Firm*—Kenneth E. Levitt, Esq.; Dorsey & Whitney LLP

(57) ABSTRACT

A flowable vertebral augmentation composition for the treatment and repair of a vertebral body defect, e.g., an osteoporotic condition, contains biocompatible, optionally osteoconductive, support elements that are resistant to deformation or fracture under the normal physiologic loads to which the repair site is subject, the support elements being incorporable into the repair site, at least one osteoinductive susbtance and an amount of biocompatible carrier sufficient to render the augmentation composition flowable, the carrier having the capacity to be cleared from the repair site.

11 Claims, 1 Drawing Sheet

VERTEBRAL AUGMENTATION COMPOSITION AND METHOD

BACKGROUND OF THE INVENTION

This invention relates to a composition and method for the treatment of porous bone such as osteoporotic bone.

The expression "porous bone" is intended herein to identify a condition of porosity and/or decreased bone mineral density that distinguishes the morphology of bone exhibiting a pathological condition from healthy bone. A common type of porous bone pathology is osteoporosis.

Osteoporosis is a pathologic state or disease involving some symptom or risk due to quantitative bone reduction exceeding a certain degree. Major symptoms are spinal kyphosis, fractures of dorsolumbar bones, vertebral centra, femoral necks, lower ends of radius, ribs, upper end of humerus, and others. In normal bone tissue, bone breakdown occurs constantly, but there is good balance between formation and resorption; osteoblasts and osteoclasts play key roles in bone formation and bone resorption, respectively. Upon deterioration of this balance, bone resorption surpasses bone formation, resulting in quantitative bone reduction.

Osteoporosis results in bone fractures in about 50% of postmenopausal women and is a leading cause of disability in an aging population. The decrease in bone mineral density and changes in architecture that accompany postmenopausal osteoporosis predisposes elderly women to fractures, particularly of the vertebral bodies. It is not elderly persons alone who suffer from this painful condition. Other individuals, such as transplant recipients, suffer fractures as a result of chronic steroid use. Current therapies include an adequate calcium and vitamin D intake as well as specific treatment with compounds such as estrogens, calcitonin and the bisphosphonates. However, each of these treatments has either troubling side effects or limited efficacy. Women fear the small increase in potential risk of breast cancer due to estrogens despite the dramatic reduction in myocardial infarctions and reduction in bone resorption. Calcitonin has a limited effect and is a protein and therefore needs to be injected or inhaled which is inconvenient. The new bisphosphonates such as alendronate have had encouraging results with an increase in bone density and decrease in fractures, however, some upper gastrointestinal irritation has been reported (Abraham et al., 1999, Mod. Pathol. Dec. 12(12): 1152-1157). Current research for new compounds has concentrated on the systemic administration of bone anabolic compounds such as parathyroid hormone (PTH) or fragments of PTH or locally acting cytokines or bone growth factors such as bone morphogenic proteins. When these therapies are unable to prevent fractures of porous bone, the victims of such fractures suffer from persistent, often excruciating pain, which significantly impairs mobility and quality of life. External bracing, analgesics, and observation may be all that is necessary for pain control in some patients, but in others, a constant requirement for narcotics can be as life altering as the fracture itself.

Vertebroplasty has been described in the literature as a method of injecting materials into vertebral bodies via a pedicle approach. Patients with various problems including osteoporosis, tumor or trauma have deficiencies of the vertebral body leading to pain or other complications. By injecting polymethyl methacrylate (bone cement) into these areas interventional radiologists or other physicians are able to avoid further subsidence of the vertebrae and alleviate pain. This procedure can be done on an outpatient basis, but currently is reserved for patients with major problems.

Vertebroplasty using injected polymethyl methacrylate suffers from the inability of the implant site to respond well to repeated stresses. Polymethyl methacrylate is a "dead" implant material which becomes brittle when subjected to repeat stresses. Bone repaired with this technique is little more than a bony shell filled with a hardened polymer.

Other methods of vertebroplastyd include the injection of granular, resorbable materials. These methods rely upon osteoinduction to provide long term strength, a process that requires time and is also susceptible to any influences that led to the initial formation of porous bone. Any bone tissue formed through osteoinduction at the implant site may be subsequently subjected to the same influences that produced the porous bone site in the first place.

Therefore, there is a need for an implant composition that is able to support physiological loads at the time of implantation and remain where placed even after it is incorporated into new tissue at the implant site. Success of the implant requires the contiguous growth of tissue to create a solid mass. The implant will be load bearing even while it is undergoing incorporation into new bony/fibrous tissue at the implant site.

Fibrous tissue, consisting primarily of fibrin and collagen proteins has been observed to infiltrate and encapsulate materials implanted into a body. The fibrous tissue can form a network of tissues that are resilient to applied forces and able to sustain physiological loads. Such a tissue network, being primarily soft tissue and containing few bone cells, would not be susceptible to those factors which lead to an increase in bone porosity and/or decrease in bone mineral density. Therefore, the implant, when eventually incorporated into fibrous tissue, would be expected to provide long term relief from the above described difficulties associated with porous bone conditions. In some applications, e.g., tumor defects, it may be advantageous to promote new bone growth at the graft site. An implant in accordance with the invention would provide load-bearing capabilities at the graft site before and during the formation of new bony tissue at the implantation site.

A flowable, and thus injectable, load-bearing composition that remains at the repair site during and after the formation of tissue at the site would be desirable.

SUMMARY OF THE INVENTION

It is an object of the invention to provide a flowable, load-bearing vertebral augmentation composition for treating a vertebrate animal having increased bone porosity and/or decreased bone mineral density.

It is a further object of the invention to provide a vertebral augmentation composition for treating osteoporotic patients at risk for the fracture of vertebra.

It is a further object of the invention to provide a method for treating bone that has fractured due to decreased bone mineral density and/or increased bone porosity.

The stated objects of the invention are not intended to be limiting in any way. Of course, further objects of the invention herein will be obvious to those skilled in the art in view of the above stated objects and the foregoing specification.

In keeping with these and related objects of the invention there is provided a flowable vertebral augmentation composition for injection within a vertebral body repair site which comprises:

a) biocompatible, optionally osteoconductive, support elements that are resistant to deformation or fracture under the normal physiologic loads to which the repair site is subject, the support elements being incorporable into the repair site;

b) at least one osteoinductive substance; and, c) an amount of biocompatible carrier sufficient to render the augmentation composition flowable, the carrier having the capacity to be cleared from the repair site.

The term "biocompatible" shall be understood to mean the absence of undesirable biological response such as the stimulation of a severe, long-lived or escalating biological response to an implant generally leading to a partial or complete loss of efficacy of the implant. Biocompatible is distinguished from a mild, transient inflammation which accompanies implantation of essentially all foreign objects into a living organism and is also associated with the normal healing response.

The term "osteoconductive" as used herein shall be understood to refer to the ability of the support elements component of the vertebral augmentation composition herein to provide biologically inert surfaces which are receptive to the growth of new host bone.

The expression "support elements" refers to discrete regularly or irregularly shaped particles, powders, granules, beads, etc., exhibiting load-bearing capability.

The expression "physiologic loads" shall be understood to refer to the mechanical loads to which vertebral bodies are characteristically subject. These loads include compressive, shear and twisting forces, shock-loading forces, and the like. For example, in the case of the lumbar spine, compressive loads of up to 10 kilonewtons have been reported. Hutton, W. C. and Adams, M. A., "Can the Lumbar Spine be Crushed in Heavy Lifting", *Spine,* pp. 586-590 (1982).

The term "osteoinductive" as used herein shall be understood to refer to the ability of a substance to recruit cells from the host which have the potential for repairing bone tissue. A material is considered to be osteoinductive if when implanted in soft tissue it leads to the formation of ectopic bone within 3 months and preferably within 28 days.

The term "flowable" shall be regarded as substantially equivalent to "injectable" and describes a compositional consistency ranging from shape-sustaining but readily deformable or malleable, e.g., a consistency characteristic of putty, paste, gel, and the like, to those that are runny and even pourable.

The expression "having the capacity to be cleared from the repair site" refers to an essential characteristic of the biocompatible carrier component of the vertebral augmentation composition, namely, that after introduction into the repair site, the carrier component will eventually leave the site, e.g., as the result of being washed away by bodily fluid and/or being metabolized and absorbed or expelled by the body.

DESCRIPTION OF THE PREFERRED EMBODIMENTS

Figure 1:
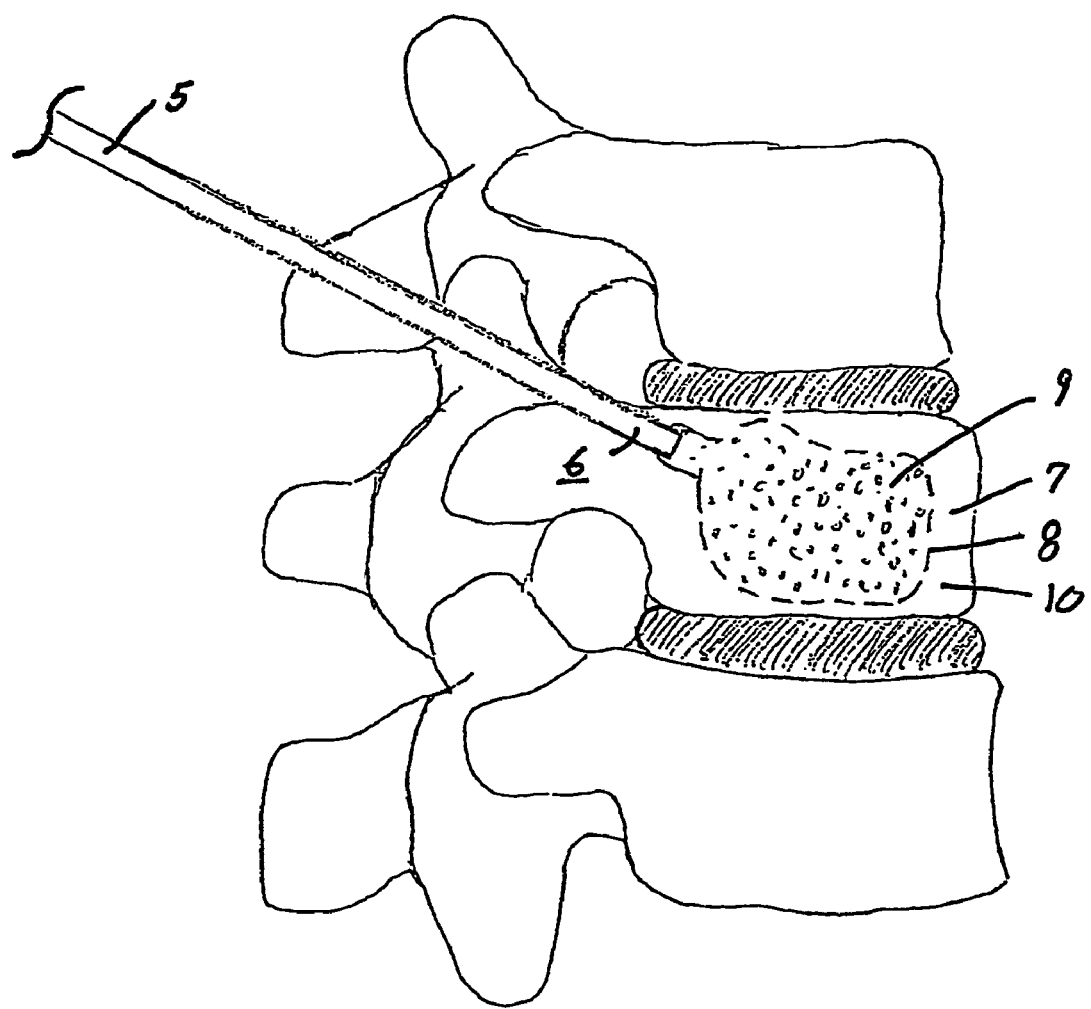
FIG. 1 is a lateral view of three vertebrae wherein the middle vertebral body is being treated with vertebral augmentation composition in accordance with the invention employing a cannula provided with an expandable bag-like containment device filled over its distal end.

The vertebral augmentation composition of this invention is useful for the treatment of individuals suffering from increased bone porosity and/or decreased bone mineral density resulting from any of a variety of conditions. The conditions leading to decrease in bone density can include, e.g., osteoporosis, osteomalacia, osteotis fibrosa, Paget's disease, bone deficiency, primary or secondary hyperparathyroidism, chronic inflammatory conditions, metastatic bone disease and osteolytic bone disease. When the condition is osteoporosis, the osteoporosis can be due to a number of conditions, e.g., age-related osteoporosis, postmenopausal osteoporosis, juvenile osteoporosis, Cushing's syndrome osteoporosis, multiple myeloma osteoporosis, leukemia osteoporosis, Turner's syndrome osteoporosis, alcohol osteoporosis, chronic liver disease osteoporosis, glucocorticoid-induced osteoporosis, chronic inflammatory disease induced osteoporosis and disuse osteoporosis. The site of decreased bone density call be trabecular bone, cortical bone, etc. When the bone site is trabecular bone, the bone can include, e.g.; vertebrae, rib, clavicle, sternum, femoral neck hip, wrist and the distal ends of the long bones.

The support elements component of the vertebral augmentation composition can be any biocompatible material that resists deformation or fracture under the physiologic loads normally experienced at the repair site. Such materials must be relatively inert as a result of which they will become incorporated into the repair site where they will tend to remain even after the ingrowth of new bony tissue. Suitable support elements include ceramics, metals, preformed solid polymers, their mixtures, and the like. Suitable ceramic support elements include bio-active glasses such as Bioglass of US Biomaterials (Alachua, Fla.), bioceramics, dentin tooth enamel, hydroxyapatite, fluorapatite and other calcium phosphate materals, sintered alumina, graphite or pyrolytic carbon, and the like. Metal support elements include those fabricated from stainless steel, cobalt-chrome alloy such as Vitalium, titanium, titanium-nickel alloy such as Nitinol, titanium-aluminum-nickel alloy, tantalum, and the like. Suitable preformed polymeric support elements include such nonbioabsorbable/nonbioerodable polymers as the polyesters, polyacrylates, polymethylmethacrylates, polyolefins, polytetrafluoroethylenes, polyurethanes, polyacetals, polyamides, and the like.

The support elements can be regularly or irregularly shaped and can vary in size over a fairly broad range. The support elements are preferably spherical, or approximately spherical, in shape and can range in size from about 50 microns up to about 4 mm and more preferably from about 250 microns up to about 2000 microns in their greatest average dimension. Other shapes and/or sizes of support elements are also suitable for use herein Thus, the support elements can be provided in the form of granules, flakes, beads, cylinders, and so forth.

Some or all of the support elements can contain cavities, they can be porous or they can be reticulated, i.e., they can contain a network of interconnecting voids or channels communicating with their surfaces, all for the purpose of encouraging and facilitating tissue ingrowth therein. Optionally, the cavities, pores, voids, channels, etc., can contain a biocompatable filler which on resorption will provide sites for infiltration by new tissue. Suitable fillers for this purpose include, e.g., glycerol, water, aqueous salts (e.g., sodium chloride or other physiologically acceptable salts or mixtures thereof), solid salts, physiologically acceptable buffer solutions, ethylene glycol, low molecular weight polyethylene glycols, polysaccharides such as starches and celluloses, bioabsorbable/bioerodable polymers, one or more osteoinductive substances as hereinafter more fully described, mixtures of two or more of the foregoing, and so forth.

The osteoinductive component of the vertebral augmentation composition herein can be selected from among any of the osteoinductive substances known in the art. Included among the useful osteoinductive substances are fully mineralized, substantially fully demineralized and/or partially demineralized bone provided as powders, grahules, threads, strips, chips, etc., derived from cortical, cancellous and/or corticocancellous allogenic, xenogenic or transgenic bone tissue (with allogenic bone being preferred), bone morphogenetic proteins (BMP) such as rhBMP-2, transforming growth factors such as TGF-beta, osteoinductive cytoknes, osteoblast cells and mixtures of two or more of the foregoing. Of the foregoing, substantially fully and partially demineralized bone, BMP, transforming growth factors and their combinations are preferred.

The biocompatible carrier component of the vertebral augmentation composition can be selected from among any of the biocompatible carriers heretofore employed in flowable osteoimplant compositions, e.g., those described in U.S. Pat. Nos. 5,073,373, 5,284,655, 5,290,558, 5,484,601, 6,030,635, the contents of which are incorporated by reference herein. These known biocompatible carriers include those which, like glycerol, are liquid in the pure or highly concentrated state at ambient temperature (15°-40° C.) or when dissolved in or combined with a liquid such as water, ethanol, aqueous ethanol, etc., provide a material which is flowable at ambient temperature. A preferred group of biocompatible carriers are the hydrated polysaccharides, e.g., unmodified and modified starches and celluloses, which, in addition to their function as carriers, conserve the osteoinductive potential of the osteoinductive component of the vertebral augmentation composition.

When tested in accordance with the Athymic Rat Model Assay ("Assay") described in Edwards et al., *Clinical Orthopaedics,* Dec. 1998, Vol. 357 (ppi 219-228), vertebral augmentation compositions containing an osteoinductive component such as demineralized bone matrix (DBM; also referred to as demineralized bone powder) and particular types of hydrated polysaccharides as carriers will provide an osteoinductive potential rating of at least 1, preferably at least 2 and more preferably at least 3 on a scale of 0 (essentially no osteoinductive activity) to 4 (maximum osteoinductive activity). Hydrated starches such as hydrated modified corn starch and hydrated celluloses such as hydrated methycellulose have been found to provide particularly good results.

The amounts of support elements, osteoinductive substance and carrier and the procedures by which these materials are combined to provide a vertebral augmentation composition in accordance with this invention can vary widely and can be readily optimized for specific kinds of support elements, osteoinductive substances and carriers employing routine experimental techniques. For example, based on the total weight of vertebral augmentation composition, the amount of support elements can range from about 20 to 90, and preferably from about 30 to about 50, weight percent of the composition. The amount of osteoinductive substance present must, of course, be an osteoinductively-effective amount. In the case of such substances as nondemineralized, partially demineralized and substantially fully demineralized bone where the osteoinductive-active substance(s) are believed to be present at relatively low levels, the amounts of these substances can be fairly high, e.g., on the order of from about 10 to about 50, and preferably from about 20 to about 40, weight percent of the composition. Where the osteoinductive substance is concentrated or is biologically active in small amounts, e.g., the case with such substances as bone morphogenetic proteins, transforming growth factors, cytokines, osteoblast cells, and the like, the useful amounts can be very small considered on a weight basis. Here, it is perhaps more appropriate to speak of a biologically or therapeutically effective amount rather than a weight amount. Optimum amounts of these and other potent osteoinductive substances can be determined employing routine experimentation. Additionally or alternatively to experimentally determining optimum amounts of these osteoinductive substances, reference may be made to the literature for amounts of these substances which have been demonstrated to be osteoinductively-effective amounts for bone defect repair applications. The amount of carrier (inclusive of any liquid or solvent that may be used to impart flowability to a particular carrier) can vary from about 20 to about 90, and preferably from about 40 to about 60, weight percent of the composition.

Preferably, the osteoinductive substance is combined with the carrier to provide a uniform premix to which the support elements are then added followed by suitable mixing to provide an overall uniform vertebral augmentation composition. Alternatively, and when employing hollow, void-containing or reticulated support elements the support elements can be soaked in a solution or dispersion of the osteoinductive substance, excess liquid removed and the osteoinductive substance-filled support elements uniformly combined with the carrier to provide the vertebral augmentation composition.

Where, in a particular vertebral augmentation composition, the support elements component exhibits a tendency to quickly or prematurely separate from the carrier component or to otherwise settle out from the composition before it can be applied to a vertebral repair site, it can be advantageous to include within the composition a substance whose thixotropic characteristics prevent or reduce this tendency. Thus, e.g., where the carrier component is glycerol and separation of the component occurs to an excessive extent where a particular application is concerned, a thickener such as a solution of polyvinyl alcohol, polyvinylpyrrolidone, cellulosic ester such as hydroxypropyl methylcellulose, carboxyl methylcellulose, pectin, food-grade texturizing agent, gelatin, dextran, collagen, starch, hydrolyzed polyacrylonitrile, hydrolyzed polyacrylamide, polyelectrolyte such as polyacrylic acid salt, hydrogels, chitosan, other materials that can suspend particles, etc., can be combined with the carrier in an amount sufficient to significantly improve the suspension-keeping characteristics of the composition.

The rheological or thixotropic behavior of the vertebral augmentation composition can be advantageously modified through the addition of one or more other materials to the composition. Thus, the composition can contain, e.g., carbon fibers, collagen fibers, tendon or ligament fibers, keratin, cellulose, hydroxy apatite and other calcium phosphate particulates, and the like, in amounts that provide good handling characteristics.

Any of a variety of medically and/or surgically useful substances can be incorporated in the vertebral augmentation composition the customary amounts during or after its preparation. Such medically and/or surgically useful substances, all types of collagen, insoluble collagen derivatives, non-collagenous proteins such as osteopontin, osteonectin, bone sialo proteins, vitronectin, thrombospondin, proteoglycans, decorin, biglycan, aggrecan, veriscan, tenascin, matrix gla protein hyaluronan; hydroxyapatite, etc., and soluble solids and/or liquids dissolved therein, e.g., antiviricides, particularly those effective against HIV and hepatitis; antimicrobials and/or antibiotics such as erythromycin, bacitracin, neomycin, penicillin, polymyxin B, tetracyclines, viomycin, chloromycetin and streptomycins, cefazolin, ampicillin, azactam, tobramycin, clindamycin and gentamycin, etc.; amino acids, peptides, vitamins, inorganic elements, inorganic compounds, cofactors for protein synthesis, hormones; soluble and insoluble components of the immune system, soluble and insoluble receptors including truncated forms, soluble, insoluble and cell surface bound ligands including truncated forms; chemokines, bioactive compounds that are endocytosed; endocrine tissue or tissue fragments; synthesizers;

enzymes such as collagenase, peptidases, oxidases, etc.; polymer cell scaffolds with parenchymal cells; angiogenic drugs and polymeric carriers containing such drugs; collagen lattices; biocompatible surface active agents; antigenic agents; cytoskeletal agents; cartilage fragments, living cells such as chondrocytes, bone marrow cells, mesenchymal stem cells, natural extracts, tissue transplants, bioadhesives, transforming growth factor (TGF-beta), insulin-like growth factor (IGF-1) (IGF-2), platelet derived growth factor (PDGF), fibroblast growth factors (FGF), vascular endothelial growth factor (VEGF), epidermal growth factor (EGF), angiogenic agents, bone promoters, cytokines, interleukins, genetic material, genes encoding bone promoting action, cells containing genes encoding bone promoting action; hormones, growth hormones such as somatotropin; bone digestors; anti-tumor agents; fibronectin; cellular attractants and attachment agents; immuno-suppressants; bone resorption inhibitors and stimulators; angiogenic and mitogenic factors; bioactive factors that inhibit or stimulate second messenger molecules; compounds that can alter the membrane potential of cells; compounds that can alter the monovalent and divalent cation/anion chemicals of cells; cell-matrix and cell-cell adhesion molecules; clotting factors; externally expanded autograft or xenograft cells, permeation enhancers, e.g., fatty acid esters such as laureate, myristate and stearate monoesters of polyethylene glycol, enamine derivatives, α-keto aldehydes, etc.; and, nucleic acids and any combination thereof. The amounts of such optionally added substances can vary widely with optimum levels being readily determined in a specific case by routine experimentation.

If the vertebral augmentation composition is not already radiopaque, it can be rendered radiopaque by the addition of compositions containing barium, tungsten, mineralized bone and the like. Agents that inhibit bone mineral loss or depress bone turnover can also be added. Such agents include, for example, stable active analogs of pyrophosphate such as those known as bisphosphonates and estrogen and analogs thereof The following table illustrates a number of flowable vertebral augmentation compositions in accordance with the present invention.

TABLE

VERTEBRAL AUGMENTATION COMPOSITIONS

| Example | Support Elements Type, Amount (wt %) | Osteoinductive Substance(s) Type, Amount (wt. %) | Carrier Type, Amount (wt %) |
|---|---|---|---|
| 1 | hydroxyapatite particles of 0.5-1.5 mm, 50 | demineralized bone matrix (DBM), 10 | modified corn starch hydrated with water or aqueous glycerol to a plastic consistency, 40 |
| 2 | sintered alumina particles of 0.5-1.5 mm, 50 | DBM, 10 BMP-2, trace amount | modified corn starch hydrated with water or aqueous glycerol to a plastic consistency, 40 |
| 3 | preformed polymethyl methacrylate particles of 1-2 mm, 40 | bonechips of 1 mm average, DBM, trace amount | aqueous glycerol, 40 |
| 4 | sintered alumina particles of 1.5-2.5 mm, 30 | bonechips of 1 mm average, 40 BMP-2, trace amount | aqueous glycerol, 30 |
| 5 | hydroxyapatite particles of 1-2 mm, 30 | DBM, 30 | aqueous hyaluronic acid, 40 |
| 6 | hydroxyapatite particles of 1-2 mm, 50 | DBM, 20 | collagen paste, 30 |

The vertebral augmentation compositions of Examples 1 and 6 can be prepared by combining the specified component(s) in any suitable order under aseptic conditions, e.g., uniformly combining the osteoinductive substance(s) and any optional component(s) with the carrier, thereafter adding the support elements, uniformly mixing the entire mass and aseptically packaging the resulting composition for future use.

The vertebral augmentation composition of the invention is intended for use in the treatment of sites exhibiting decreased bone density. Once the site of decreased bone density is located utilizing methods well known in the art, e.g., bone density scans, radiographic imaging, medical history, a suitable amount of vertebral augmentation composition is injected into the bone site utilizing methods well known in the art, e.g., through a needle or cannula, e.g., a Jamshidi® 11 gauge bone marrow biopsy/aspiration needle. In a preferred embodiment of the invention, a percutaneous vertebroplasty technique as described by Jensen et al. *Diagnostic Imaging,* pp. 68-72, September 1997, the contents of which are incorporated herein by reference, is used to inject the composition into the vertebra. This technique, a fluoroscopically guided transpedicular approach, is especially safe and rapid.

When the condition leading to the decrease in bone mineral density has progressed to an advanced stage, compression fractures of the affected area may occur. In such a case, operative intervention may be required to facilitate the effective use of the composition of the invention herein. Operative procedures would include anterior or posterior decompression and stabilization with placement of such internal fixation devices as screws, plates, cages or rods. Once the implant site has been first cleaned out and restored to the proper size as in conventional, polymer-based vertebral augmentation, the composition of the invention is injected such that it substantially completely fills the vertebral repair site. When the composition is radiopaque, filing of the graft site can be monitored fluoroscopically. Upon withdrawal of the needle or cannula from the implant site, the opening through which the composition is injected can be plugged, if desired, with a suitable material such as a bone chip, polymethyl methacrylate bone cement, etc.

In cases where the vertebral body repair site is too damaged to adequately contain the vertebral augmentation composition of this invention, a flexible and/or expandable containment device can be fitted to the distal end of the needle or, as shown in FIG. 1, the cannula, through which the composition is injected into the repair site. As shown in FIG. 1, distal end 6 of cannula 5 inserted in vertebral body 7 is provided with a tightly fitting flexible and/or expandable bag-like or balloon-like containment device 8. As vertebral augmentation composition 9 is injected into containment device 8, the latter expands to fill repair site 10.

Preferably, containment device 8 is constructed from a resorbable material, numerous types of which are known, such that the device will eventually be absorbed by the body and permit uninterrupted tissue penetration into the filler. The device can be of woven construction or it can be made of porous sheet. The device is of such construction that it will readily expand as the vertebral augmentation composition is injected therein and as a result, fill up or occupy the repair site.

Among the useful construction materials for containment device 8 are woven fabrics such as the woven dacron fabrics that have been used as vascular graft materials. These and similar graft materials act as scaffolds which are first coated with fibrin and subsequently covered with granulation tissue and then encapsulated with fibrous tissue. As a containment device manufactured with such materials becomes associated with fibrous tissue it also assists in providing support for physiologic loads incurred at the vertebral repair site.

EXAMPLE 7

The site of decreased bone density in a vertebral body of a human subject ("repair site") is located utilizing methods well known in the art, e.g., bone density scans, radiographic imaging, medical history. A vertebral augmentation composition according to the invention, e.g., one of the compositions of Examples 1-6, is then injected into the repair site utilizing methods well known in the art, e.g., through a needle or cannula, e.g., a Jamshidi®11 gauge bone marrow biopsy/aspiration needle, either embodscopically or percutaneously. In a preferred embodiment of the invention, the percutanous vertebroplasty technique of Jensen et al., *Diagnostic Imaging*, pp. 68-72, September 1997, is used to inject the composition into the vertebral repair site. Within about 2 weeks, the carrier will have substantially cleared from the repair site and generalized healing of the bone will be observed. Cellular activity indicative of fibrous and/or bony tissue formation will also be observed around the support elements. In time, there will be full revascularization of the repair site and formation of mature tissue structures. The supports elements will have been incorporated within the new tissue structures with little or no degradation of the elements.

What is claimed is:

1. A vertebral augmentation device which comprises:
   a) a flowable vertebral augmentation composition for injection within a vertebral body repair site, the flowable composition comprising:
      (i) biocompatible, optionally osteoconductive, support elements that are resistant to deformation or fracture under the normal physiologic loads to which the repair site is subject, the support elements being incorporable into the repair site, wherein the support elements are fabricated from ceramic, metal the metal being stainless steel, cobalt-chrome alloy, titanium-nickel alloy, titanium-nickel-aluminum alloy, tantalum or combination thereof, preformed solid polymer, or combination thereof
      (ii) an amount of biocompatible carrier sufficient to render the augmentation composition flowable, the carrier having the capacity to be cleared from the repair site; and,
   b) a containment device, the containment device accepting the flowable vertebral augmentation composition.

2. A vertebral augmentation device which comprises:
   a) a flowable vertebral augmentation composition for injection within a vertebral body repair site, the flowable composition comprising:
      (i) biocompatible, optionally osteoconductive, support elements that are resistant to deformation or fracture under the normal physiologic loads to which the repair site is subject, the support elements being incorporable into the repair site;
      (ii) an amount of biocompatible carrier sufficient to render the augmentation composition flowable, the carrier having the capacity to be cleared from the repair site wherein the carrier is glycerol; and,
   b) a containment device, the containment device accepting the flowable vertebral augmentation composition.

3. A vertebral augmentation device which comprises:
   a) a flowable vertebral augmentation composition for injection within a vertebral body repair site, the flowable composition comprising:
      (i) biocompatible, optionally osteoconductive, support elements that are resistant to deformation or fracture under the normal physiologic loads to which the repair site is subject, the support elements being incorporable into the repair site;
      (ii) an amount of biocompatible carrier sufficient to render the augmentation composition flowable, the carrier having the capacity to be cleared from the repair site wherein the carrier contains a hydrated polysaccharide; and,
   b) a containment device, the containment device accepting the flowable vertebral augmentation composition.

4. A vertebral augmentation device which comprises:
   a) a flowable vertebral augmentation composition for injection within a vertebral body repair site, the flowable composition comprising:
      (i) biocompatible, optionally osteoconductive, support elements that are resistant to deformation or fracture under the normal physiologic loads to which the repair site is subject, the support elements being incorporable into the repair site;
      (ii) an amount of biocompatible carrier sufficient to render the augmentation composition flowable, the carrier having the capacity to be cleared from the repair site wherein the carrier contains a hydrated unmodified or modified starch or cellulose; and,
   b) a containment device, the containment device accepting the flowable vertebral augmentation composition.

5. A method for treating a defect site associated with a vertebral body which comprises introducing within the defect site of a vertebral augmentation device comprising:
   a) a vertebral augmentation composition comprising:
      (i) biocompatible, optionally osteoconductive, support elements that are resistant to deformation or fracture under the normal physiologic loads to which the repair site is subject, the support elements being incorporable into the repair site; and
      (ii) an amount of biocompatible carrier sufficient to render the augmentation composition flowable, the carrier having the capacity to be cleared from the repair site; and,
   b) a containment device, the containment device accepting the vertebral augmentation composition;
   wherein the vertebral augmentation composition is introduced into the defect site though a needle or cannula and wherein the containment device is fitted on a distal end of the needle or cannula, the containment device occupying the vertebral repair site as the containment device is filled with vertebral augmentation composition.

6. The method of claim 5 wherein the containment device is constructed from a resorbable material.

7. A vertebral augmentation device which comprises:
   a) a flowable vertebral augmentation composition for injection within a vertebral body repair site, the flowable composition comprising:

(i) biocompatible, optionally osteoconductive, support elements that are resistant to deformation or fracture under the normal physiologic loads to which the repair site is subject, the support elements being osteoinductive demineralized bone and being incorporable into the repair site;

(ii) an amount of biocompatible carrier sufficient to render the augmentation composition flowable, the carrier having the capacity to be cleared from the repair site; and, b) a containment device, the containment device accepting the flowable vertebral augmentation composition.

8. A method for treating a defect site associated with a vertebral body which comprises introducing within the defect site of a vertebral augmentation device comprising:

a) a vertebral augmentation composition comprising:

(i) biocompatible, optionally osteoconductive, support elements that are resistant to deformation or fracture under the normal physiologic loads to which the repair site is subject, the support elements being incorporable into the repair site; and (ii) an amount of biocompatible carrier sufficient to render the augmentation composition flowable, the carrier having the capacity to be cleared from the repair site; and, (iii) at least one osteoinductive substance; and b) a containment device, the containment device accepting the vertebral augmentation composition.

9. The method of claim 8, wherein the osteoinductive substance is demineralized bone.

10. A vertebral augmentation device which comprises:

a) a flowable vertebral augmentation composition for injection within a vertebral body repair site, the flowable composition comprising:

(i) biocompatible, optionally osteoconductive, support elements that are resistant to deformation or fracture under the normal physiologic loads to which the repair site is subject, the support elements being incorporable into the repair site;

(ii) an amount of biocompatible carrier sufficient to render the augmentation composition flowable, the carrier having the capacity to be cleared from the repair site; and, b) a containment device, the containment device accepting the flowable vertebral augmentation composition, wherein the containment device is constructed from a resorbable material.

11. A method for treating a defect site associated with a vertebral body which comprises introducing within the defect site of a vertebral augmentation device comprising:

a) a vertebral augmentation composition comprising:

(i) biocompatible, optionally osteoconductive, support elements that are resistant to deformation or fracture under the normal physiologic loads to which the repair site is subject, the support elements being incorporable into the repair site; and (ii) an amount of biocompatible carrier sufficient to render the augmentation composition flowable, the carrier having the capacity to be cleared from the repair site; and, b) a containment device, the containment device accepting the vertebral augmentation composition, wherein the containment device is constructed form a resorbable material.

* * * * *

UNITED STATES PATENT AND TRADEMARK OFFICE
CERTIFICATE OF CORRECTION

PATENT NO.       : 7,399,739 B2                                              Page 1 of 1
APPLICATION NO.  : 10/399423
DATED            : July 15, 2008
INVENTOR(S)      : Lawrence A. Shimp It is certified that error appears in the above-identified patent and that said Letters Patent is hereby corrected as shown below:

On the Title Page, insert Item [60]

[60] -- Domestic Priority Application Data: Provisional application no. 60/242,852, filed on October 24, 2000 --

| Column | Line | | Should Read |
|---|---|---|---|
| 4 | 11 | "femoral neck hip," | -- femoral neck, hip, -- |
| 5 | 4 | "cytoknes" | -- cytokines -- |
| 5 | 28 | "(ppi 219-228)" | -- (pp. 219-228) -- |

Signed and Sealed this

First Day of September, 2009

David J. Kappos
*Director of the United States Patent and Trademark Office*